(12) United States Patent
Hudetz

(10) Patent No.: US 6,271,177 B1
(45) Date of Patent: Aug. 7, 2001

(54) SELECTIVE HERBICIDAL COMPOSITION

(75) Inventor: Manfred Hudetz, Rheinfelden (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/005,050

(22) Filed: Jan. 9, 1998

Related U.S. Application Data

(63) Continuation-in-part of application No. PCT/EP96/02857, filed on Jun. 29, 1996.

(51) Int. Cl.⁷ .............................. A01N 47/36; A01N 59/00
(52) U.S. Cl. ...................... 504/212; 504/213; 504/214; 504/215; 504/124; 504/125
(58) Field of Search ..................... 504/124, 125, 504/212, 213, 214, 215

(56) References Cited

U.S. PATENT DOCUMENTS

| | | | |
|---|---|---|---|
| 2,921,847 | 1/1960 | Knell et al. | 71/1 |
| 4,551,531 | 11/1985 | Meyer et al. | 544/320 |
| 4,881,965 | 11/1989 | Yamamoto et al. | 71/92 |
| 5,532,203 | * 7/1996 | Fory et al. | 504/105 |

FOREIGN PATENT DOCUMENTS

| | | |
|---|---|---|
| 0 084 020 | 7/1983 | (EP) . |
| 0 318 602 | 6/1989 | (EP) . |
| 0 388 873 | 9/1990 | (EP) . |
| 0 592 660 | 4/1994 | (EP) . |
| 54 105 299 | 8/1979 | (JP) . |

OTHER PUBLICATIONS

The Pesticide Manual, Tenth Edition, BCPC, Editor Clive Tomlin, 1994, pp. 34, 85, 180, 211, 486, 584, 586, 587, 696, 701, 734, 829, 865, 904, 931, 976, 1005, and 1010.
The Pesticide Manual, Tenth Edition, BCPC, Editor Clive Tomlin, 1994, p. 462.
Derwent Abstract 70786B/39 (of JP 5 4 105 229), 1979.

* cited by examiner

Primary Examiner—Sabiha Qazi
(74) Attorney, Agent, or Firm—William A. Teoli, Jr.

(57) ABSTRACT

A selective herbicidal composition for controlling grasses and weeds in crops of cultivated plants comprising, in addition to customary formulation assistants,
  a) a herbicide selected from the group consisting of sulfonyl ureas, sulfonamides and imidazolinones; and
  b) a water-soluble iron compound.

11 Claims, No Drawings

SELECTIVE HERBICIDAL COMPOSITION

This is a continuation-in-part application of International application PCT/EP 96/02857 filed Jun. 29, 1996.

The present invention relates to a novel selective herbicidal composition for controlling grasses and weeds in crops of cultivated plants, which composition comprises a herbicide and an iron compound and protects the cultivated plants, but not the weeds, from the phytotoxic action of the herbicide, and to the use of said composition for controlling weeds in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall.

To counteract this problem and similar ones, the proposal has already been made to use different compounds e.g. as antidote or safener which are able to antagonise the harmful action of the herbicide on the cultivated plant, i.e. to protect the cultivated plant while leaving the herbicidal action on the weeds to be controlled virtually unimpaired. It has, however, been found that the proposed compounds often have a very specific action, not only with respect to the cultivated plants but also to the herbicide, and in some cases also subject to the mode of application.

Surprisingly, it has now been found that a variable amount of a combination of herbicidal acetolactate synthase inhibitors (ALS inhibitors) with specific iron compounds develops an increased selectivity of the respective ALS inhibitors for the crops of cultivated plants, which combination is able to control the majority of weeds that occur preferably in crops of cultivated plants by the preemergence as well as, in particular, by the postemergence method without substantially damaging the cultivated plant.

Accordingly, the invention proposes a selective herbicidal composition comprising, in addition to customary inert formulation assistants such as carriers, solvents and wetting agents, a mixture of a) a herbicidally effective acetolactate synthase inhibitor (ALS inhibitor) selected from the group consisting of sulfonyl ureas, sulfonamides and imidazolinones; and b) a water-soluble iron compound.

In the compositions of this invention it is preferred to use a) the herbicidally effective acetolactate synthase inhibitors of the sulfonyl urea group which are characterised in that they correspond to formula A

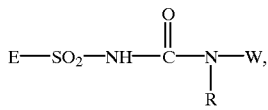
(A)

wherein

E is a group of formula

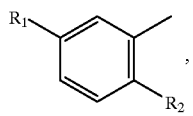
($E_{01}$)

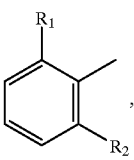
($E_1$)

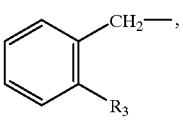
($E_2$)

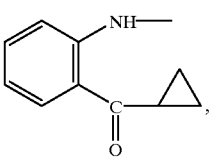
($E_3$)

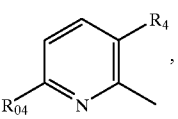
($E_4$)

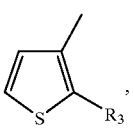
($E_5$)

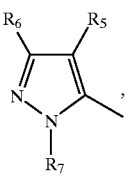
($E_6$)

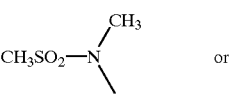
($E_7$)

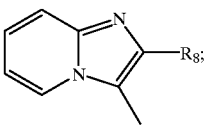
($E_8$)

W is a group of formula

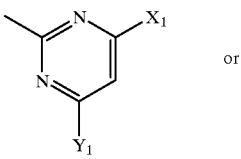
($W_1$)

or

-continued

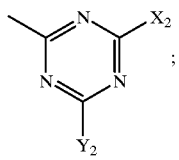
(W₂)

R and $R_1$ are each independently of the other hydrogen, methyl or methoxy;

$R_2$ is chloro, nitro, —CH₂CH₂CF₃, —OCH₂CH₂OCH₃, —OCH₂CH₂Cl, —COO—C₁alkyl, —COO—C₂alkyl or

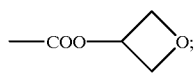

$R_3$ is —COO—C₁alkyl or —COO—C₂alkyl;
$R_4$ is —COOCH₃, —CF₃, —OCHF₂, —OCH₂CF₃, —OCH₂CHClF, —CON(CH₃)₂ or —SO₂C₂H₅;
$R_{04}$ is hydrogen or —CF₃;
$R_5$ is —COO—C₁alkyl or —COO—C₂alkyl or the group of formula

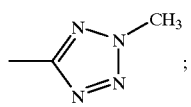

$R_6$ is hydrogen or chloro;
$R_7$ is methyl or the group of formula

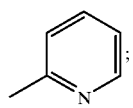

$R_8$ is chloro or —SO₂C₂H₅;
$X_1$ is chloro, methyl, methoxy or —OCHF₂;
$Y_1$ is methyl, methoxy or —OCHF₂;
$X_2$ is methyl, methoxy, ethoxy, —CF₃ or —N(CH₃)₂; and
$Y_2$ is —CF₃, methoxy, —OCH₂CF₃ or —NHCH₃, and the salts of those compounds;

those herbicidally effective acetolactate synthase inhibitors of the sulfonamide group which are characterised in that they correspond to formula C

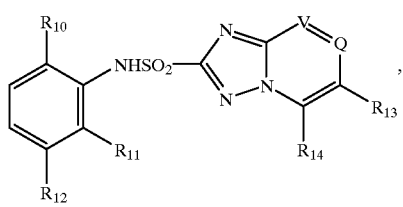
(C)

wherein
$R_{10}$ is fluoro or chloro;
$R_{11}$ is fluoro, chloro or a —COOCH₃ group;
$R_{12}$ is hydrogen or methyl;
$R_{13}$ is hydrogen or fluoro;
$R_{14}$ is hydrogen or methoxy;
V is nitrogen or a C—OC₂H₅ group; and
Q is nitrogen or a C—CH₃ or C—OCH₃ group; or to formula $C_1$

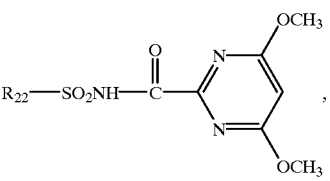
(C₁)

wherein
$R_{22}$ is $C_1$–$C_{10}$alkyl, $C_1$–$C_{10}$alkyl which is substituted by halogen, $C_3$–$C_8$cycloalkyl, cyano or oxiranyl, $C_2$–$C_8$alkenyl, $C_2$–$C_8$haloalkenyl or amino; and those herbicidally effective acetolactate synthase inhibitors of the imidazolinone group which are characterised in that they correspond to formula D

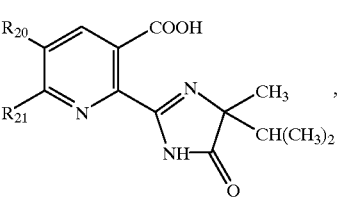
(D)

wherein
$R_{20}$ is hydrogen, methyl, ethyl or a —CH₂—OCH₃ group;
$R_{21}$ is hydrogen; or
$R_{20}$ and $R_{21}$, taken together, form a —CH=CH—CH=CH— group; and b) water-soluble iron compounds which are characterised in that they correspond to formula B $$[Fe^{II,III}\text{-}Z] \tag{B}$$

wherein
$Fe^{II,III}$ is the element iron having the oxidation number +2 (II) or +3 (III); and
Z is a mono- or polyvalent anion of inorganic or organic acids H-Z.

Compounds of formula A which are preferably used in the composition of this invention are those, wherein E is a group of formula

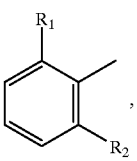
(E₁)

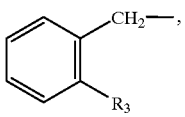  (E₂)

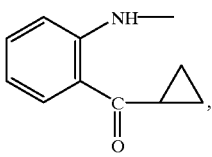  (E₃)

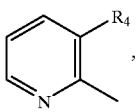  (E₄)

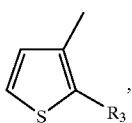  (E₅)

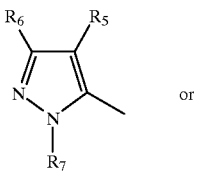 or  (E₆)

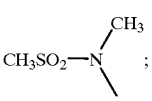  (E₇)

W is a group of formula

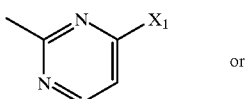 or  (W₁)

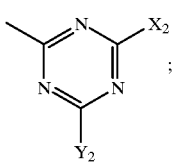  (W₂)

R and R₁ are each independently of the other hydrogen or methyl;

R₂ is chloro, nitro, —CH₂CH₂CF₃, —OCH₂CH₂OCH₃, —OCH₂CH₂Cl, —COO—C₁alkyl, —COO—C₂alkyl or

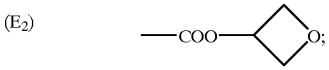

R₃ is —COO—C₁alkyl or —COO—C₂alkyl;

R₄ is —CF₃, —OCHF₂, —OCH₂CF₃, —OCH₂CHClF, —CON(CH₃)₂ or —SO₂C₂H₅;

R₅ is —COO—C₁alkyl or —COO—C₂alkyl or the group of formula

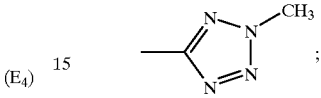

R₆ is hydrogen or chloro;

R₇ is methyl or the group of formula

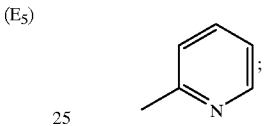

X₁ is chloro, methyl, methoxy or —OCHF₂;
Y₁ is methyl, methoxy or —OCHF₂;
X₂ is methyl, methoxy, ethoxy or —N(CH₃)₂; and
Y₂ is —CF₃, methoxy, —OCH₂CF₃ or —NHCH₃, and the salts of those compounds.

The sulfonyl urea compounds of formula A used according to this invention are known, inter alia, from "The Pesticide Manual", Tenth Edition, 1994, Editor C. Tomlin, pages 34, 85, 180, 211, 701, 734, 829, 865, 904, 931, 976, 1005 and 1010; EP-A-0 084 020, EP-A-0 318 602 and EP-A-0 388 873, and some are commercially available (see Tables 1 and 2).

The invention also includes the salts that the compounds of formula A can form with in principle any bases that are capable of abstracting an acid hydrogen atom, e.g. in the —SO₂—NH—CO— grouping. Amines, hydrides, hydroxides, alcoholates, hydrogen carbonates and carbonates of alkali metal and alkaline earth metals, especially of sodium, potassium, magnesium and calcium, have proved especially advantageous in that connection.

The sulfonamides of formula C and C₁ used according to this invention and their preparation are known, inter alia, from "The Pesticide Manual", Tenth Edition, 1994, Editor C. Tomlin, pages 486 and 696, and from EP-A-0 592 680, and some are commercially available (see Tables 5 and 6).

The imidazolinones of formula D and their preparation are known, inter alia, from "The Pesticide Manual", Tenth Edition, 1994, Editor C. Tomlin, pages 584, 586 and 587, and some are commercially available (see Table 7).

The water-soluble iron compounds of formula B are iron salts or iron chelates, wherein the iron may have the oxidation number +2 (II: divalent iron) or +3 (III: trivalent iron). The appertaining anions Z can carry one or more than one negative charge. They can be formed from the corresponding inorganic or organic acids H-Z by abstracting the acid hydrogen atom. Suitable are, for example, mineral acids, such as hydrochloric acid, sulfuric acid or nitric acid, organic acids, preferably polyacids, such as (HOOC—CH₂—)₂ and

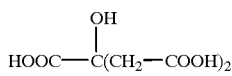

and, particularly preferably, organic acids, the iron chelates ($Fe^{II,III}$-Z) of which are distinguished by high stability even at basic pH (pH values>7), typically ethylenediamine tetracetic acid $(HOOC-CH_2)_2NCH_2CH_2N(CH_2-COOH)_2$ (ETA), N,N'-ethylenebis[2-(2-hydroxyphenyl)glycine]

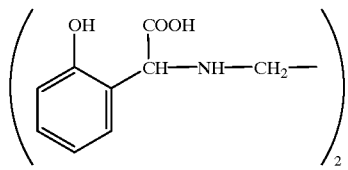

(EDDHA), diethylenetriaminepentacetic acid $(HOOC-CH_2)_2NCH_2CH_2N(CH_2-COOH)CH_2CH_2N(CH_2-COOH)_2$ (DTPA) and N-(2-hydroxyethyl)ethylenediaminetriacetic acid $HO-CH_2CH_2N(CH_2-COOH)CH_2CH_2N(CH_2-COOH)_2$ (HEDTA).

The iron chelates of formula B are obtained from iron salts and mono- or polyvalent acids HZ, such as are also used in the preparation of commercial iron chelates. The preparation of such iron chelates and their use as micronutrients in agriculture is disclosed, inter alia, in US-A-2 921 847.

Commercial forms of the above-mentioned iron chelates ($Fe^{II,III}$-Z) react according to the nature of Z acidically in aqueous solutions or emulsions, e.g. in accordance with $[Fe^{II,III}$-Z$(-COOH)_m]$, or neutrally, e.g. in accordance with $[Fe^{II,III}$-Z$]$ or $[Fe^{II,III}$-Z$(-COO^{\ominus}Me^{n\oplus})_m]$, wherein m is 1, 2, 3, 4 or 5 and $Me^{n\oplus}$ is the cation of a monovalent (n=1) or polyvalent (n=2, 3, 4, or 5) organic or, preferably, inorganic base, typically

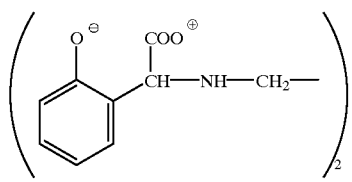

$Fe^{3\oplus}Na^{\oplus}$=Fe-EDDHA (Sequestrene 138).

The invention also relates to a method of selectively controlling weeds in crops of cultivated plants, which comprises treating said cultivated plants, the seeds or seedlings or the crop area thereof, concurrently or separately, with a herbicidally effective amount of an ALS inhibitor selected from the group consisting of sulfonyl ureas, sulfonamides and imidazolinones, and a water-soluble iron compound.

Particularly preferred compounds of formula A are those, wherein $R_2$ is $-COO-C_1$alkyl, $-COO-C_2$alkyl or

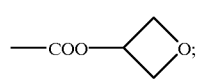

$R_3$ is $-COO-C_1$alkyl or $-COO-C_2$alkyl; $X_1$ is chloro or methyl; $Y_1$ is methyl or methoxy; $X_2$ is methyl; and $Y_2$ is methoxy.

Preferred compounds of formula A for use in the composition of this invention are those, wherein E is a group of formula

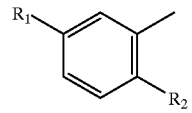  (E01)

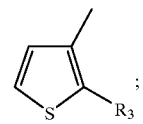  (E5)

W is a group of formula

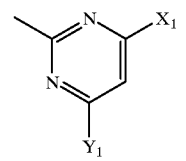  (W1)

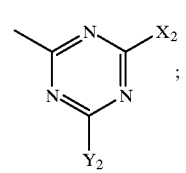  (W2)

R is hydrogen; and $R_1$, $R_2$, $R_3$, $X_1$, $X_2$, $Y_1$ and $Y_2$ are as defined for formula A.

Among these compounds of formula A those are particularly preferred, wherein E is a group of formula

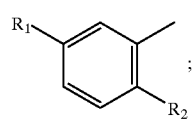  (E01)

W is a group of formula

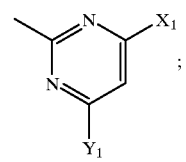  (W1)

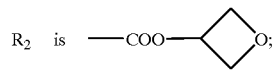

and $X_1$ and $Y_1$ are methyl.

Preferred compounds of formula B for use in the composition of this invention are characterised in that group Z is an anion of EDTA, EDDHA, DTPA or HEDTA.

Among these compounds of formula B those are particularly preferred, wherein Z is an anion of EDDHA or DTPA.

Suitable compositions according to this invention are distinguished in that they comprise a compound of formula A, wherein E is a group of formula

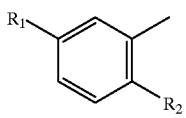

or

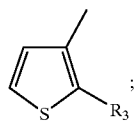

W is a group of formula

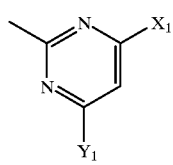

or

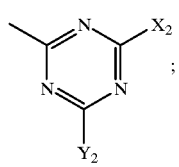

$R_2$ is —COO—$C_1$alkyl —COO—$C_2$alkyl or

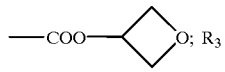

is —COO—$C_1$alkyl or —COO—$C_2$alkyl; $X_1$ is chloro or methyl; $Y_1$ is methyl or methoxy; $X_2$ is methyl; and $Y_2$ is methoxy; and a compound of formula B, wherein Z is an anion of EDTA, EDDHA, DTPA or HEDTA.

Among these compositions those are particularly suitable, wherein, in the compounds of formula B, group Z is an anion of EDDHA or DTPA.

Particularly suitable compositions are also those, wherein, in the compounds of formula I, substituent E is a group of formula (E$_{01}$)

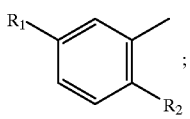

substituent W is a group of formula (W$_1$)

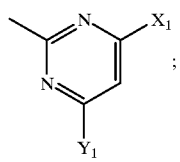

$R_2$ is 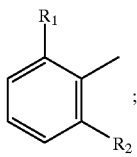

and $X_1$ and $Y_1$ are methyl, and group Z in the compound of formula B is an anion of EDDHA or DTPA.

Particularly suitable compositions are also those, wherein, in the compounds of formula A, substituent E is a group of formula (E$_1$)

[structure with $R_1$ and $R_2$]

substituent W is a group of formula (W$_1$)

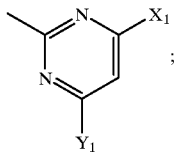

$R_2$ is —COO—[oxetane]O;

and $X_1$ and $Y_1$ are methyl, and group Z in the compound of formula B is an anion of EDDHA or DTPA.

Among these compositions those are very particularly suitable, wherein R and $R_1$ are hydrogen; and group Z in the compound of formula B is an anion of EDDHA.

Suitable cultivated plants which can be protected by the water-soluble iron compounds against the harmful action of the aforementioned herbicides are sugar beet, cereal, maize, rice, cotton wool and, preferably, soybean.

The weeds to be controlled can be monocot as well as dicot weeds.

Crop areas will be understood as meaning the areas already under cultivation with the cultivated plants or seeds thereof, as well as the areas intended for cropping with said cultivated plants.

Depending on the end use, the water-soluble iron compound can be incorporated in the soil before or after sowing. It can, however, also be applied by itself or together with the herbicide, preferably postemergence. Treatment of the plants with the iron compound can therefore in principle be carried out irrespective of the time of application of the herbicide. Treatment can, however, also be carried out by simultaneous application of the herbicide and the iron compound (e.g. as tank mixture). Preemergence treatment includes treatment of the cropping area before sowing as well as treatment of the cropping areas after sowing but before the plants have started to grow.

The concentration of iron compound with respect to the herbicide will depend substantially on the mode of application. Where a field treatment is carried out either by using a tank mixture with a combination of iron compound and herbicide or by separate application of iron compound and herbicide, the ratio of herbicide to iron compound will usually be from 1:100 to 100:1, preferably from 1:20 to 20:1 and, most preferably. from 1:5 to 5:1.

In field treatment it is usual to apply 0.001 to 5.0 kg/ha, preferably 0.001 to 1.0 kg/ha of iron compound.

The concentration of herbicide is usually in the range from 0.001 to 0.5 kg/ha, but will preferably be from 0.005 t o 0.2 kg/ha.

The compositions of this invention are suitable for all methods of application commonly used in agriculture, including preemergence application and, preferably, postemergence application.

For application, it is preferred to process the iron compounds or combinations of these iron compounds with the herbicides of formulae A, C, $C_1$ and D, convenienty together with the customary assistants of formulation technology, typically to emulsifiable concentrates, coatable pastes, directly sprayable or dilutable solutions, dilute emulsions, wettable powders, soluble powders, dusts, granulates or microcapsules. The formulations are prepared in known manner, conveniently by homogeneously mixing and/or grinding the active ingredients with liquid or solid formulation assistants, typically solvents or solid carriers. Surface-active compounds (surfactants) may additionally be used for preparing the formulations.

Suitable solvents may typically be: aromatic hydrocarbons, preferably the fractions containing 8 to 12 carbon atoms such as xylene mixtures or substituted naphthalenes; phthalates such as dibutyl or dioctyl phthalate; aliphatic hydrocarbons such as cyclohexane or paraffins; alcohols and glycols and their ethers and esters such as ethanol, diethylene glycol, 2-methoxneth anol or 2-ethoxyethanol; ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soy bean oil; or water.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residues.

Depending on the iron compounds and, where appropriate, also on the herbicide, suitable surfactants are nonionic, cationic and/or anionic surfactants having good emulsifying, dispersing and wetting properties. Tensides will also be understood to include surfactant mixtures.

Suitable anionic surfactants may be so-called water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts.

More often, however, so-called synthetic surfactants are used, especially fatty alcohol sulfonates, fatty alcohol sulfates, sulfonated benzimidazole derivatives or alk ylaryl sulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of liyninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylaryl sulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 ethylene oxide or phospholipids, are also suitable.

Nonionic surfactants are preferably polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxyethanols, castor oil polyglycol ether, polyadducts of polypropylene and polyethylene oxide, tributylphenoxy polyethoxyethanol, polyethylene glycol and octylphenoxy polyethoxyethanol.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl) ethylammonium bromide.

The surfactants customarily employed in the art of formulation and which can also be used in the compositions of this invention are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, Miinchen/Wien, 1981 and M. and J. Ash, "Encyclopedia of Surfactants", Vol I-III, Chemical Publishing Co., New York, 1980–81.

The agrochemical formulations will usually contain from 0.1 to 99% by weight, preferably from 0.1 to 95% by weight, of iron compound or of a compound mixture of iron compound and herbicide, from 1 to 99.9% by weight, preferably from 5 to 99.8% by weight of a solid or liquid formulation assistant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilisers, antifoams, viscosity regulators, binders, tackifiers or other active ingredients, e.g. additional sulfonyl ureas and further herbicidal acetolacetate synthase inhibitors (ALS inhibitors), typically additional sufonamides and imidazolinones as well as further metal chelates of, for example, calcium, magnesium, zinc or manganese and also further trace elements which are import ant for the physiology of the plant.

Different methods and techniques may suitably be used for applying the water-soluble iron compounds or compositions containing them for selectively protecting cultivated plants from the harmful effects of acetolacetate synthase inhibitors, for example the following:

i) Application as a tank mixture

A liquid formulation of a mixture of iron compound and herbicide (reciprocal ratio from 10:1 to 1:100) is used, the concentration of herbicide being from 0.001 to 0.2 kg/ha. This tank mixture is applied before or after sowing.

ii) Application in the furrow

The iron compound formulated as emulsifiable concentrate, wettable powder or granulate is applied to the open furrow in which the seeds have been sown. After covering the furrow, the herbicide is applied preemergence in conventional manner.

iii) Controlled release of safener

A solution of the compound of formula B is applied to mineral granulate substrates or polymerised granulates (urea/formaldehyde) and allowed to dry. A coating may additionally be applied (coated granulates) which permits controlled release of the safener over a specific period of time.

The invention is illustrated in more detail by the following non-limitative Examples.

Formulation Examples for mixtures of sulfonyl urea herbicides of formula A, sulfonamide herbicides of formula C and $C_1$, imidazolinone herbicides of formula D and iron compounds of formula B used according to this invention (throughout, percentages are by weight)

| F1. Emulsifiable concentrates | a) | b) | c) | d) |
|---|---|---|---|---|
| compound mixture | 5% | 10% | 25% | 50% |
| calcium dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$—$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| compound mixture | 5% | 10% | 50% | 90% |
| dipropylene glycol methyl ether | — | 20% | 20% | — |
| polyethylene glycol 400 | 20% | 10% | — | — |
| N-methyl-2-pyrrolidone | — | — | 30% | 10% |
| mixture of aromatic hydrocarbons $C_9$—$C_{12}$ | 75% | 60% | — | — |

The solutions are suitable for use as microdrops.

| F3. Wettable powders | a) | b) | c) | d) |
|---|---|---|---|---|
| compound mixture | 5% | 25% | 50% | 80% |
| sodium ligninsulfate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound mixture is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| compound mixture | 0.1% | 5% | 15% |
| highly dispersed silica | 0.9% | 2% | 2% |
| inorganic carrier (Ø 0.1–1 mm) e.g. $CaCO_3$ or $SiO_2$ | 99.0% | 93% | 83% |

The compound mixture is dissolved in methylene chloride, the solution is sprayed on to the carrier, and the solvent is removed under vacuum.

| F5. Coated granulates | a) | b) | c) |
|---|---|---|---|
| compound mixture | 0.1% | 5% | 15% |
| polyethylene glycol 200 | 1.0% | 2% | 3% |
| highly dispersed silica | 0.9% | 1% | 2% |
| inorganic carrier (Ø 0.1–1 mm) e.g. $CaCO_3$ or $SiO_2$ | 98.0% | 92% | 80% |

The finely ground compound mixture is uniformly applied in a mixer to the carrier substrate moistened with polyethylene glycol. Non-dusty coated granulates are obtained in this manner.

| F6. Extruder granulates | a) | b) | c) | d) |
|---|---|---|---|---|
| compound mixture | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound mixture is mixed with the adjuvants and the mixture is moistened with water. This mixture is extruded and then dried in a stream of air.

| F7. Dusts | a) | b) | c) |
|---|---|---|---|
| compound mixture | 0.1% | 1% | 5% |
| talcum | 39.9% | 49% | 35% |
| kaolin | 60.0% | 50% | 60% |

Ready for use dusts are obtained by mixing the the active ingredient with the carriers on a suitable mill.

| F8. Suspension concentrates | a) | b) | c) | d) |
|---|---|---|---|---|
| compound mixture | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is intimately mixed with the adjuvants to give a suspension concentrate from which suspensions of any desired concentration can be prepared by dilution with water.

Illustrative examples of particularly suitable compounds of formula A are given in Tables 1 and 2 below.

TABLE 1

Herbicides of formula A $$E-SO_2-NH-\overset{\overset{O}{\|}}{C}-\underset{\underset{R}{|}}{N}-W \qquad (A)$$

| Cmpd No. | E | $R_1$ | $R_2$ | R | W | $X_{1\ or\ 2}$ | $Y_{1\ or\ 2}$ | Common name or reference lit. |
|---|---|---|---|---|---|---|---|---|
| 1.1 | $E_1$ | H | Cl | H | $W_2$ | $CH_3$ | $OCH_3$ | chlorosulfurone |
| 1.2 | $E_1$ | H | $COOCH_3$ | $CH_3$ | $W_2$ | $CH_3$ | $OCH_3$ | tribenurone |
| 1.3 | $E_1$ | H | $COOCH_3$ | H | $W_2$ | $CH_3$ | $OCH_3$ | metsulfurone |
| 1.4 | $E_1$ | H | $OCH_2CH_2OCH_3$ | H | $W_2$ | $OCH_3$ | $OCH_3$ | cinosulfurone |
| 1.5 | $E_1$ | H | $OCH_2CH_2Cl$ | H | $W_2$ | $CH_3$ | $OCH_3$ | triasulfurone |
| 1.6 | $E_1$ | H | $CH_2CH_2CF_3$ | H | $W_2$ | $CH_3$ | $OCH_3$ | prosulfurone |
| 1.7 | $E_1$ | H | $COOCH_3$ | H | $W_1$ | $OCHF_2$ | $OCHF_2$ | primisulfurone |
| 1.8 | $E_1$ | H | $COOCH_3$ | H | $W_1$ | $OCHF_2$ | $CH_3$ | EP-A-0 084 020 |
| 1.9 | $E_1$ | H | $NO_2$ | H | $W_1$ | $OCHF_2$ | $CH_3$ | EP-A-0 084 020 |
| 1.10 | $E_1$ | H | $COOCH_3$ | H | $W_1$ | $CH_3$ | $CH_3$ | sulfometurone |
| 1.11 | $E_1$ | H | $COOC_2H_5$ | H | $W_1$ | $OCH_3$ | Cl | chloroimurone |
| 1.12 | $E_1$ | H | COOCH | H | $W_2$ | $OC_2H_5$ | $NHCH_3$ | ethametsulfurone |
| 1.13 | $E_1$ | $CH_3$ | $COOCH_3$ | H | $W_2$ | $OCH_2CF_3$ | $N(CH_3)_2$ | triflusulfurone |
| 1.14 | $E_1$ | H | COO—⟨oxetane⟩ | H | $W_1$ | $CH_3$ | $CH_3$ | EP-A-0 496 701 |
| 1.15 | $E_1$ | H | $COOCH_3$ | H | $W_2$ | $CF_3$ | $OCH_3$ | EP-A-0 388 873 |

TABLE 2

Herbicides of formula A $$E-SO_2-NH-\overset{\overset{O}{\|}}{C}-\underset{\underset{R}{|}}{N}-W$$

| Cmpd No. | E | R | W | Common name or reference lit. |
|---|---|---|---|---|
| 2.1 | 2-(COOCH₃)-benzyl (—CH₂— attached to phenyl with ortho COOCH₃) | H | 2-methyl-4,6-dimethoxypyrimidin-... (pyrimidine with OCH₃, OCH₃) | bensulfurone |
| 2.2 | 2-(cyclopropylcarbonyl)anilino (—NH— attached to phenyl with ortho C(O)-cyclopropyl) | H | 2-methyl-4,6-dimethoxypyrimidin-... (pyrimidine with OCH₃, OCH₃) | cyclosulfamurone |

TABLE 2-continued
Herbicides of formula A
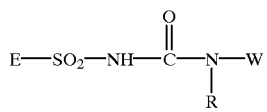
| Cmpd No. | E | R | W | Common name or reference lit. |
|---|---|---|---|---|
| 2.3 | 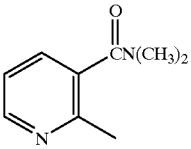 | H | 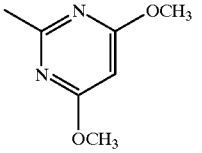 | nicosulfurone |
| 2.4 | 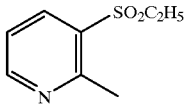 | H | 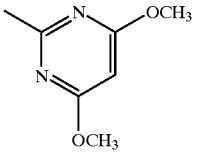 | rimsulfurone |
| 2.5 | 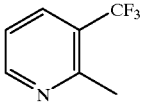 | H | 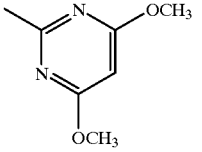 | fluzasulfurone |
| 2.6 | 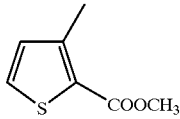 | H | 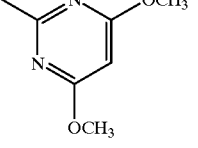 | thiphensulfurone |
| 2.7 | 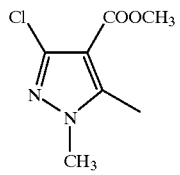 | H | 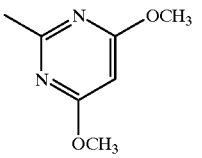 | halosulfurone |
| 2.8 | 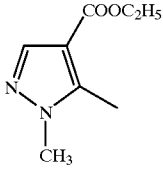 | H | 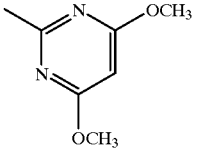 | pyrazosulfurone (NC 311) |
| 2.9 | 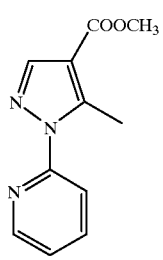 | H | 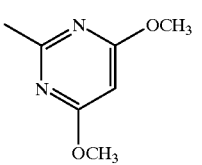 | EP-A-0 318 602 (NC 330) |

TABLE 2-continued

Herbicides of formula A

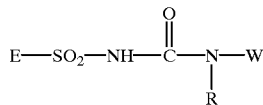

| Cmpd No. | E | R | W | Common name or reference lit. |
|---|---|---|---|---|
| 2.10 | 1,5-dimethylpyrazol-4-yl-(2-methyltetrazol-5-yl) group | H | 2-methyl-4,6-dimethoxypyrimidin-2-yl | azimsulfurone |
| 2.11 | CH₃SO₂—N(CH₃)₂ | H | 2-methyl-4,6-dimethoxypyrimidin-2-yl | amidosulfurone |
| 2.12 | 6-CF₃-2-methyl-3-(COOCH₃)pyridyl | H | 2-methyl-4,6-dimethoxypyrimidin-2-yl | flupyrsulfurone |
| 2.13 | 3-methyl-2-(SO₂C₂H₅)imidazo[1,2-a]pyridinyl | H | 2-methyl-4,6-dimethoxypyrimidin-2-yl | sulfosulfurone |
| 2.14 | 3-(OCH₂CF₃)-2-methylpyridyl | H | 2-methyl-4,6-dimethoxypyrimidin-2-yl | |
| 2.15 | [3-(OCH₂CF₃)pyridin-2-yl-SO₂—N—C(O)—NH—(4,6-dimethoxypyrimidin-2-yl)]⁻ Na⁺ | | | |

Illustrative examples of particularly suitable iron compounds of formula B are given in Table 3 below.

TABLE 3

Iron compounds of formula B
$[Fe^{II,III}-Z]$ (B)
$[Fe^{II,III}-Z]$ (commerical forms)

| | |
|---|---|
| 3.1 | $FeCl_3$ |
| 3.2 | $FeSO_4$ |
| 3.3 | Fe-EDTA |
| 3.4 | Fe-EDDHA (=Sequestrene 138) |
| 3.5 | Fe-DTPA (=Sequestrene 330) |
| 3.6 | Fe-HEDTA |

Illustrative examples of particularly suitable mixture combinations of the compounds of Tables 1 and 2 and of Table 3 are given in Table 4 below.

TABLE 4

Mixture combinations of the herbicide of formula A
(Tables 1 and 2) and the iron compound of formula B (Table 3)

| Cmpd No. | Herbicide A | Iron compound B |
|---|---|---|
| 4.1 | 1.11 | 3.3 |
| 4.2 | 1.11 | 3.4 |
| 4.3 | 1.11 | 3.5 |
| 4.4 | 1.11 | 3.6 |
| 4.5 | 2.6 | 3.3 |
| 4.6 | 2.6 | 3.4 |
| 4.7 | 2.6 | 3.5 |
| 4.8 | 2.6 | 3.6 |
| 4.9 | 1.14 | 3.1 |
| 4.10 | 1.14 | 3.2 |
| 4.11 | 1.14 | 3.3 |
| 4.12 | 1.14 | 3.4 |
| 4.13 | 1.14 | 3.5 |
| 4.14 | 1.14 | 3.6 |

Illustrative examples of particularly suitable compounds of formulae C, $C_1$ and D are given in Tables 5, 6 and 7 below.

TABLE 5

Herbicides of formula C

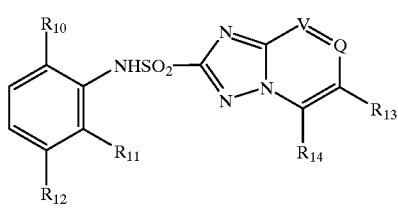

(C)

| Comp No. | $R_{10}$ | $R_{11}$ | $R_{12}$ | $R_{13}$ | $R_{14}$ | V | Q | Common name or reference lit. |
|---|---|---|---|---|---|---|---|---|
| 5.1 | F | F | H | H | H | N | C-Me | flumetsulam |
| 5.2 | Cl | Cl | Me | H | OMe | N | C-OMe | metosulam |
| 5.3 | Cl | $COOCH_3$ | H | F | H | C-OEt | N | cloransulam |

TABLE 6

Herbicides of formula $C_1$

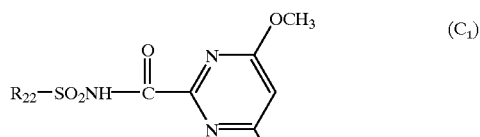

($C_1$)

| Cmpd No. | $R_{22}$ |
|---|---|
| 6.1 | $-CH_2-CH=CHCl$ (Z) |
| 6.2 | $-CH_2-CH=CHCl$ (E) |
| 6.3 | $-CH_2-CCl=CH_2$ |
| 6.4 | $-CH_2-CCl=CHCl$ |
| 6.5 | $-CH_2-C(CH_3)=CHCl$ |
| 6.6 | $-CH_2-CBr=CH_2$ |
| 6.7 | $-CH_2-CCl=CHCH_3$ |
| 6.8 | $-CH_2-CH=CHBr$ |
| 6.9 | $-CH_2-CHCl-CH_2Cl$ |
| 6.10 | $-CH_2-\overset{O}{\underset{\triangle}{}}$ |
| 6.11 | $-CH_2-C(CH_3)_3$ |
| 6.12 | $-CH_2-\triangle$ |
| 6.13 | $-CH_2-CH_2CN$ |
| 6.14 | $-CH_2-CH=CClCH_3$ |
| 6.15 | $-CH_2-CH=C(CH_3)_2$ |
| 6.16 | $-CH_2-CH_2-C(CH_3)_3=CH_2$ |
| 6.17 | $-CH_2-CH=CCl_2$ |
| 6.18 | $-CH=CH-CH_2CH_3$ |
| 6.19 | $-NH2$ |
| 6.20 | $-CH_2-CH=CHCl$ |
| 6.21 | $-CH_2-C(CH_3)=CH_2$ |

The compounds 6.1 to 6.21 and their preparation are described in EP-A-0 592 680. Compounds 6.3 to 6.21 are mixtures of (Z) and (E) isomers.

TABLE 7

Herbicides of formula D $$R_{20} \text{—pyridine structure with COOH, imidazolinone substituent} \quad (D)$$

| Cmpd No. | $R_{20}$ | $R_{21}$ | Common name or reference lit. |
|---|---|---|---|
| 7.1 | —CH=CH—CH=CH— | | Imazaquin (Scepter ®) |
| 7.2 | Et | H | Imazethapyr (Pursuit ®) |
| 7.3 | H | H | Imazapyr |
| 7.4 | Me | H | Imazamethapyr |
| 7.5 | —CH$_2$OMe | H | Imazamox (Bolero ®) |

The following Examples illustrate the ability of the water-soluble iron compounds to protect cultivated plants from the phytotoxic action of the ASL inhibitors used according to this invention and selected from the group consisting of sulfonyl urea, sulfonamide and imidazolinone herbicides and to increase the selectivity of the sulfonyl urea, sulfonamide and imidazolinone herbicides used according to this invention.

BIOLOGICAL EXAMPLES

Example B1

Postemergence Herbicidal Action (Contact Herbicide)

The test plants are raised under greenhouse conditions in plastic pots to the 2–3 leaf stage. The growth substrate is standard soil. To the test plants are applied at this stage the herbicides by themselves or also in admixture. Application is made with an aqueous suspension of the test substances, prepared from a 25% wettable powder formulation (Example F3, b)), in 500 l of water/ha, with a standard spray nozzle. The rates of application are governed by the optimum rates determined according to field and greenhouse conditions.

The tests are evaluated after 21 days (percentage of action, 100=plant withered, 0=no phytotoxic action).

Test plants: soybean, Amaranthus, Chenopodium.

The results obtained from this test show that by using the iron compounds of formula B the selectivity of the herbicides of formulae A, C, C$_1$ and D against the cultivated plants can be markedly enhanced while the herbicidal activity against the weeds is retained.

Tables B1 to B8 illustrate this.

Table B1: Postemergence herbicidal action of compound No. 1.14 by itself and in combination with in each case 1000 g/ha of Sequestrene 138; rate of application 60 g, 90 g and 120 g of active substance/ha.

| Test plants | Cmpd No. 1.14 [g ai/ha] | | | Cmpd No. 1.14 [g ai/ha] | | | +Sequestrene 138 |
|---|---|---|---|---|---|---|---|
| | 120 | 90 | 60 | 120 | 90 | 60 | 1000 g/ha |
| Soybean | 50 | 40 | 20 | 20 | 10 | 10 | |
| Amaranthus | | 98 | 98 | | 98 | 98 | |
| Chenopodium | | 98 | 90 | | 98 | 98 | |

Table B2: Postemergence herbicidal action of compound No. 1.14 by itself and in combination with in each case 1000 g/ha of FeCl$_2$; rate of application 60 g, 90 g and 120 g of active substance/ha.

| Test plants | Cmpd No. 1.14 [g ai/ha] | | | Cmpd No. 1.14 [g ai/ha] | | | +FeCl$_2$ |
|---|---|---|---|---|---|---|---|
| | 120 | 90 | 60 | 120 | 90 | 60 | 1000 g/ha |
| Soybean | 50 | 40 | 20 | 20 | 10 | 10 | |
| Amaranthus | | 98 | 98 | | 98 | 98 | |
| Chenopodium | | 98 | 90 | | 98 | 95 | |

Table B3: Postemergence herbicidal action of compound No. 1.14 by itself and in combination with in each case 1000 g/ha of Fe-EDTA; rate of application 60 g, 90 g and 120 g of active substance/ha.

| Test plants | Cmpd No. 1.14 [g ai/ha] | | | Cmpd No. 1.14 [g ai/ha] | | | +Fe-EDTA |
|---|---|---|---|---|---|---|---|
| | 120 | 90 | 60 | 120 | 90 | 60 | 1000 g/ha |
| Soybean | 50 | 40 | 20 | 30 | 30 | 20 | |
| Amaranthus | | 98 | 98 | | 98 | 98 | |
| Chenopodium | | 98 | 90 | | 98 | 98 | |

Table B4: Postemergence herbicidal action of compound No. 1.11 by itself and in combination with in each case 1000 g/ha of Sequestrene 330; rate of application 8 g, 15 g and 30 g of active substance/ha.

| Test plants | Cmpd No. 1.11 [g ai/ha] | | | Cmpd No. 1.11 [g ai/ha] | | | +Sequestrene 330 |
|---|---|---|---|---|---|---|---|
| | 30 | 15 | 8 | 30 | 15 | 8 | 1000 g/ha |
| Soybean | 85 | 70 | 50 | 35 | 35 | 20 | |
| Amaranthus | 60 | 60 | 60 | 60 | 60 | 60 | |
| Chenopodium | 30 | 30 | 30 | 30 | 20 | 20 | |

Table B5: Postemergence herbicidal action of compound No. 2.6 by itself and in combination with in each case 1000 g/ha of Sequestrene 330; rate of application 8 g, 15 g and 30 g of active substance/ha.

Table B6: Postemergence herbicidal action of compound No. 7.2 by itself and in combination with in each case 1000 g/ha of Sequestrene 330; rate of application 70 g and 140 g of active substance/ha.

|  | Cmpd No. 7.2 [g ai/ha] | | Cmpd No. 7.2 [g ai/ha] | | +Sequestrene 330 |
|---|---|---|---|---|---|
| Test plants | 140 | 70 | 140 | 70 | 1000 g/ha |
| Soybean | 70 | 35 | 35 | 35 | |
| Amaranthus | 70 | 70 | 60 | 50 | |
| Chenopodium | 50 | 0 | 35 | 30 | |

Table B7: Postemergence herbicidal action of compound No. 7.1 by itself and in combination with in each case 1000 g/ha of Sequestrene 330; rate of application 90 g and 180 g of active substance/ha.

|  | Cmpd No. 7.1 [g ai/ha] | | Cmpd No. 7.1 [g ai/ha] | | +Sequestrene 330 |
|---|---|---|---|---|---|
| Test plants | 180 | 90 | 180 | 90 | 1000 g/ha |
| Soybean | 35 | 10 | 15 | 10 | |
| Amaranthus | 60 | 60 | 70 | 60 | |
| Chenopodium | 30 | 20 | 20 | 20 | |

Table B8: Postemergence herbicidal action of compound No. 6.1 by itself and in combination with in each case 1000 g/ha of Seauestrene 330; rate of application 15 g, 30 g and 60 g of active substance/ha.

|  | Cmpd No. 6.1 [g ai/ha] | | | Cmpd No. 6.1 [g ai/ha] | | | +Sequestrene 330 |
|---|---|---|---|---|---|---|---|
| Test plants | 60 | 30 | 15 | 60 | 30 | 15 | 1000 g/ha |
| Soybean | 60 | 55 | 45 | 45 | 40 | 35 | |
| Amaranthus | 60 | 60 | 60 | 80 | 70 | 60 | |
| Chenopodium | 95 | 90 | 90 | 90 | 80 | 80 | |

The increased selectivity of compound No. 2.6 (Harmony®) in combination with Sequestrene 330, shown in Table B5, is particularly surprising because the cited active ingredient does not act as a herbicide in soybean. This indicates an increase in the selectivity of herbicidal acetolactate synthase inhibitors (ALS inhibitors) in cultivated plants in the presence of water-soluble iron compounds.

The same results are obtained by formulating the compounds of formulae A, C, $C_1$, D and B according to the Examples F1, F2 and F4 to F8.

What is claimed is:

1. A selective herbicidal composition, comprising, in addition to customary inert formulation assistants, a mixture of a) a herbicide selected from the group consisting of sulfonyl ureas, and b) safening amount of a water-soluble iron compound.

2. A composition according to claim 1, wherein a) the herbicide of the sulfonyl urea group corresponds to formula A (A)

$$E-SO_2-NH-\overset{\overset{O}{\|}}{C}-\underset{R}{N}-W,$$

wherein

E is a group of formula

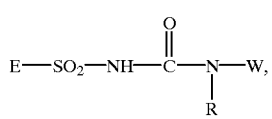
($E_{01}$)

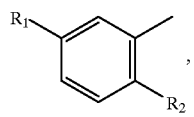
($E_1$)

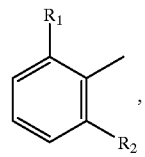
($E_2$)

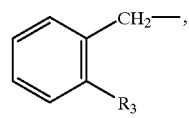
($E_3$)

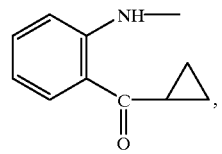
($E_4$)

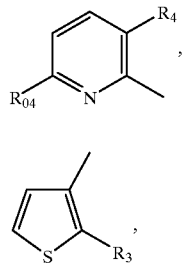
($E_5$)

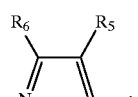
($E_6$)

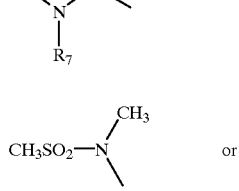
($E_7$)

or

-continued

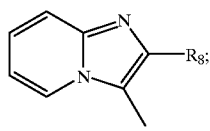
(E8)

W is a group of formula

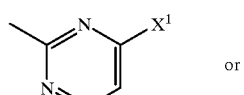
(W1)

or

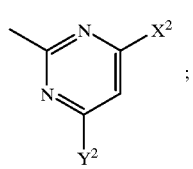
(W2)

R and R₁ are each independently of the other hydrogen, methyl or methoxy;

$R_2$ is chloro, nitro, —CH₂CH₂CF₃, —OCH₂CH₂OCH₃, —OCH₂CH₂Cl, —COO—C₁alkyl, —COO—C₂alkyl or

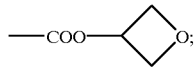

$R_3$ is —COO—C₁alkyl or —COO—C₂alkyl;
$R_4$ is —COOCH₃, —CF₃, —OCHF₂, —OCH₂CF₃, —OCH₂CHClF, —CON(CH₃)₂ or —SO2C₂H₅;
$R_{04}$ is hydrogen or —CF₃;
$R_5$ is —COO—C₁alkyl or —COO—C₂alkyl or the group of formula

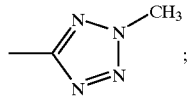

$R_6$ is hydrogen or chloro;
$R_7$ is methyl or the group of formula

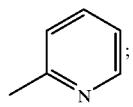

$R_8$ is chloro or —SO₂C₂H₅;
$X_1$ is chloro, methyl, methoxy or —OCHF₂;
$Y_1$ is methyl, methoxy or —OCHF₂;
$X_2$ is methyl, methoxy, ethoxy, —CF₃ or —N(CH₃)₂; and
$Y_2$ is —CF₃, methoxy, —OCH₂CF₃ or —NHCH₃, and the salts of those compounds;
b) the water-soluble iron compound corresponds to formula B $$[Fe^{II,III}\text{-}Z]$$ (B), wherein $Fe^{II,III}$ is the element iron having the oxidation number +2 (II) or +3 (III); and Z is a mono- or polyvalent anion of inorganic or organic acids H-Z.

3. A composition aording to claim 2, wherein, in the compounds of formula A, E is a group of formula

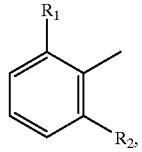
(E1)

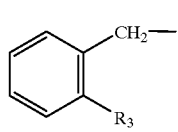
(E2)

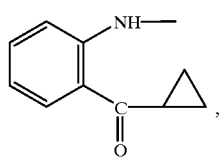
(E3)

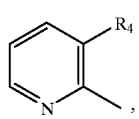
(E4)

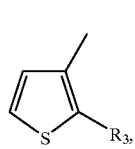
(E5)

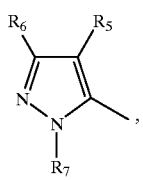
(E6)

or

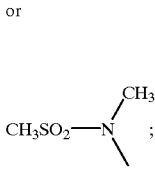
(E7)

W is a group of formula

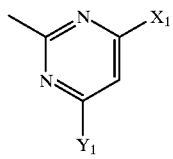
(W₁)

or

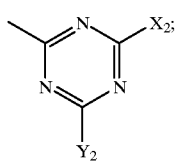
(W₂)

R and R₁ are each independently of the other hydrogen or methyl;

R₂ is chloro, nitro, —CH₂CH₂CF₃, —OCH₂CH₂OCH₃, —OCH₂CH₂Cl, —COO—C₁alkyl, —COO—C₂alkyl or

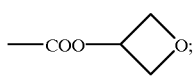

R₃ is —COO—C₁alkyl or —COO—C₂alkyl;
R₄ is —CF₃, —OCHF₂, —OCH₂CF₃, —OCH₂CHClF, —CON(CH₃)₂ or —SO₂C₂H₅;
R₅ is —COO—C₁alkyl or —COO—C₂alkyl or the group of formula

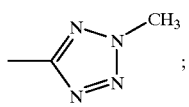

R₆ is hydrogen or chloro;
R₇ is methyl or the group of formula

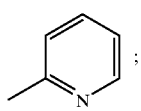

X₁ is chloro, methyl, methoxy or —OCHF₂;
Y₁ is methyl, methoxy or —OCHF₂;
X₂ is methyl, methoxy, ethoxy or —N(CH₃)₂; and
Y₂ is —CF₃, methoxy, —OCH₂CF₃ or —NHCH₃, and the salts of those compounds.

4. A composition according to claim 3, wherein R₂ is —COO—C₁alkyl, —COO—C₂alkyl or

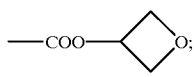

R₃ is —COO—C₁alkyl or —COO—C₂alkyl; X₁ is chloro or methyl; Y₁ is methyl or methoxy; X₂ is methyl; and Y₂ is methoxy.

5. A composition according to claim 2, wherein, in the compounds of formula A, substituent E is a group of formula

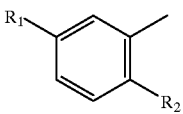
(E₀₁)

or

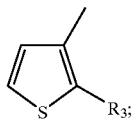
(E₅)

substituent W is a group of formula

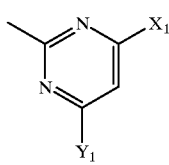
(W₁)

or

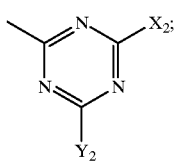
(W₂)

R is hydrogen; and R₁, R₂, R₃, X₁, X₂, Y₁ and Y₂ are as defined in claim 2.

6. A composition according to claim 5, wherein E is a group of formula

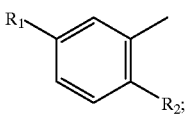
(E₀₁)

W is a group of formula

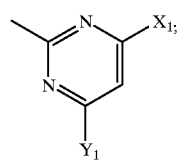
(W₁)

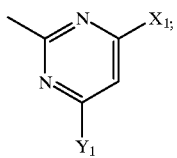
(W₁)

-continued

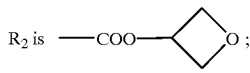

and $X_1$ and $Y_1$ are methyl.

7. A composition according to claim 2, comprising a compound of formula A, wherein E is a group of formula

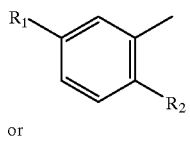
(E$_{01}$)

or

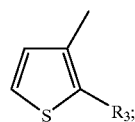
(E$_5$)

W is a group of formula

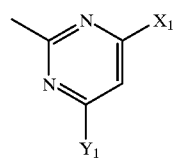
(W$_1$)

or

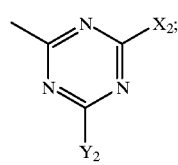
(W$_2$)

$R_2$ is —COO—C$_1$alkyl, —COO—C$_2$alkyl or

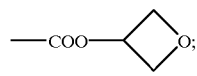

$R_3$ is —COO—C$_1$alkyl or —COO—C$_2$alkyl; $X_1$ is chloro or methyl; $Y_1$ is methyl or methoxy; $X_2$ is methyl; and $Y_2$ is methoxy; and a compound of formula B, wherein Z is an anion of EDTA, EDDHA, DTPA or HEDTA.

8. A composition according to claim 7, wherein, in the compound of formula A, substituent E is a group of formula

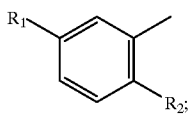
(E$_{01}$)

substituent W is a group of formula

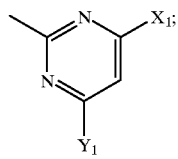
(W$_1$)

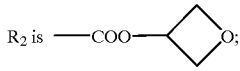

and $X_1$ and $Y_1$ are methyl.

9. A composition according to claim 3, wherein, in the compound of formula A, substituent E is a group of formula

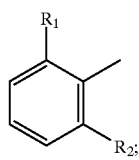
(E$_1$)

substituent W is a group of formula

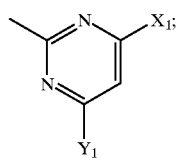
(W$_1$)

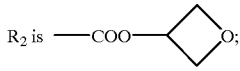

and $X_1$ and $Y_1$ are methyl.

10. A composition according to claim 9, wherein R and $R_1$ are hydrogen.

11. A composition according to claim 1, comprising further adjuvants such as stabilisers, antifoams, viscosity regulators, binders, tackifiers or other active ingredients as well as metal chelates and further trace elements.

* * * * *